(12) United States Patent
Hashimoto

(10) Patent No.: US 10,266,476 B2
(45) Date of Patent: Apr. 23, 2019

(54) (METH)ACRYLATE MANUFACTURING METHOD

(71) Applicant: TOAGOSEI CO., LTD., Tokyo (JP)

(72) Inventor: Naoki Hashimoto, Aichi (JP)

(73) Assignee: TOAGOSEI CO., LTD., Tokyo (JP)

( * ) Notice: Subject to any disclaimer, the term of this patent is extended or adjusted under 35 U.S.C. 154(b) by 0 days.

(21) Appl. No.: 15/565,030

(22) PCT Filed: Mar. 14, 2016

(86) PCT No.: PCT/JP2016/058030
§ 371 (c)(1),
(2) Date: Oct. 6, 2017

(87) PCT Pub. No.: WO2016/163208
PCT Pub. Date: Oct. 13, 2016

(65) Prior Publication Data
US 2018/0118658 A1 May 3, 2018

(30) Foreign Application Priority Data

Apr. 10, 2015 (JP) ................. 2015-080645

(51) Int. Cl.
| | | |
|---|---|---|
| *B01J 20/10* | (2006.01) | |
| *B01J 20/16* | (2006.01) | |
| *B01J 31/02* | (2006.01) | |
| *B01J 31/12* | (2006.01) | |
| *B01J 31/24* | (2006.01) | |
| *B01J 35/00* | (2006.01) | |
| *C07B 61/00* | (2006.01) | |
| *C07C 67/03* | (2006.01) | |
| *C07C 67/56* | (2006.01) | |
| *C07C 69/54* | (2006.01) | |

(52) U.S. Cl.
CPC .............. *C07C 67/03* (2013.01); *B01J 20/10* (2013.01); *B01J 20/16* (2013.01); *B01J 31/0212* (2013.01); *B01J 31/0237* (2013.01); *B01J 31/0244* (2013.01); *B01J 31/0267* (2013.01); *B01J 31/12* (2013.01); *B01J 31/24* (2013.01); *B01J 35/0006* (2013.01); *C07C 67/56* (2013.01); *B01J 2231/49* (2013.01); *B01J 2531/004* (2013.01); *C07B 61/00* (2013.01)

(58) Field of Classification Search
CPC ........ B01J 20/10; B01J 20/16; B01J 31/0212; B01J 31/0237; B01J 31/0244; B01J 31/0267; B01J 31/12; B01J 31/24; B01J 35/0006; B01J 2231/49; B01J 2531/004; C07C 67/03; C07C 69/54; C07B 61/00
See application file for complete search history.

(56) References Cited

U.S. PATENT DOCUMENTS

2017/0204044 A1    7/2017    Hashimoto et al.

FOREIGN PATENT DOCUMENTS

| CN | 103274940 | * | 9/2013 |
|---|---|---|---|
| JP | S53-105417 A | | 9/1978 |
| JP | 2001-316328 A | | 11/2001 |
| JP | 2001316328 | * | 11/2001 |
| JP | 2006-016322 A | | 1/2006 |
| JP | 46-56351 B2 | | 3/2011 |
| JP | 48-11109 B2 | | 11/2011 |
| WO | 2015/159611 A1 | | 10/2015 |

OTHER PUBLICATIONS

English translation of JP2001316328, pp. 1-25 (Year: 2001).*
English Translation of CN103274940, pp. 1-8 (Year: 2013).*
Maegawa et al., "Additive Effect of N-Heteroaromatics of Transesterification Catalyzed by Tetranuclear Zinc Cluster", ACS Catalysis vol. 1 No. 10 pp. 1178-1182, 2011.
International Search Report dated May 16, 2016, mailed Jun. 14, 2016.
English Translation of International Search Report dated May 16, 2016, mailed Jun. 14, 2016.

* cited by examiner

*Primary Examiner* — Pancham Bakshi
*Assistant Examiner* — Mark R Luderer
(74) *Attorney, Agent, or Firm* — Norris McLaughlin, PA

(57) ABSTRACT

The present invention provides a (meth)acrylate manufacturing method characterized in that when manufacturing a (meth)acrylate by an ester exchange reaction between an alcohol and a monofunctional (meth)acrylate using catalyst A and catalyst B together, contact treatment of the ester exchange reaction product with adsorbent C is performed. Catalyst A: One or more kinds of compounds selected from a group consisting of cyclic tertiary amines with an azabicyclo structure and salts or complexes thereof, amidine and salts or complexes thereof, compounds with a pyridine ring and salts or complexes thereof, phosphines and salts or complexes thereof, and compounds with a tertiary diamine structure and salts or complexes thereof. Catalyst B: One or more kinds of compounds selected from a group consisting of compounds comprising zinc. Adsorbent C: One or more kinds of compounds selected from a group consisting of oxides and hydroxides comprising at least one of magnesium, aluminum and silicon.

10 Claims, 1 Drawing Sheet

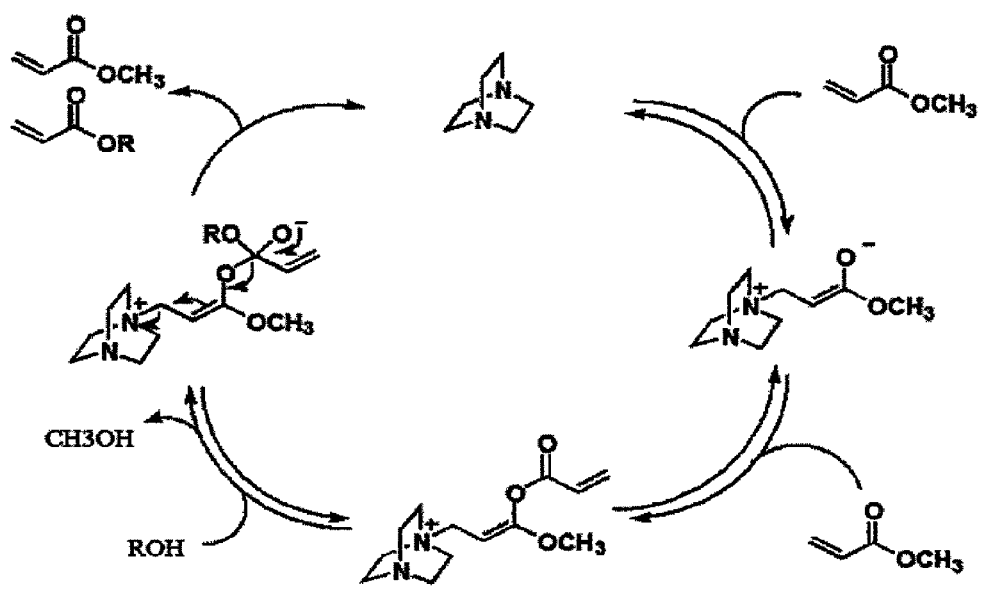
REACTION INTERMEDIATE

(METH)ACRYLATE MANUFACTURING METHOD

This application is a 371 application of PCT/JP2016/058030 filed Mar. 14, 2016, which claims foreign priority benefits under 35 U.S.C. § 119 of Japanese Application No. 2015-080645 filed Apr. 10, 2015, the disclosures of each of which are incorporated by reference herein in their entirety.

TECHNICAL FIELD

The present invention relates to a method for producing a (meth)acrylate. More specifically, it relates to a method for producing a (meth)acrylate, which includes subjecting an alcohol and a monofunctional (meth)acrylate to a transesterification reaction to obtain a (meth)acrylate. In particular, it relates to a method for removing the catalyst used in the reaction.

BACKGROUND ART (Meth)acrylates are cured by being irradiated with active energy rays such as ultraviolet rays and electron beams or by being heated, and they are thus used in large quantities as a crosslinking component of blended materials such as paints, inks, adhesives, optical lenses, fillers, and molding materials or a reactive diluent component.

In particular, polyfunctional (meth)acrylates having three or more (meth)acryloyl groups are used in large quantities as a blending component of hard coat paints since the cured products thereof exhibit high hardness and excellent abrasion resistance.

As such polyfunctional (meth)acrylates, trimethylolpropane tri(meth)acrylate, glycerol tri(meth)acrylate, pentaerythritol tri(meth)acrylate, pentaerythritol tetra(meth)acrylate, ditrimethylolpropane tetra(meth)acrylate, dipentaerythritol tetra(meth)acrylate, dipentaerythritol penta(meth)acrylate, dipentaerythritol hexa (meth)acrylate, tripentaerythritol octa (meth)acrylate, and the like are known.

These (meth)acrylates are produced by an esterification reaction using the corresponding alcohol and the corresponding (meth)acrylic acid as raw materials and sulfonic acid (see Patent Literature 1) as a catalyst or a transesterification reaction using the corresponding alcohol and the corresponding monofunctional (meth)acrylate as raw materials and an organotin compound (see Patent Literature 2) as a catalyst. In addition, with regard to the transesterification reaction, a method is known in which an organophosphorus compound and a zinc compound are concurrently used as a catalyst (see Patent Literature 3).

The catalyst used in the production of these (meth)acrylates is removed by a purification operation after the reaction. In a case in which the catalyst is insufficiently removed, however, the storage stability and thermal stability of the (meth)acrylate obtained are poor, a polymerization reaction and a hydrolysis reaction take place during storage, and a polymer and an acid component such as (meth)acrylic acid are generated in some cases.

Curing unevenness and turbidity of the (meth)acrylate containing a polymer are caused so that the (meth)acrylate cannot be suitably used in the optical lens application in which uniformity and optical transparency are regarded as important. In addition, the (meth)acrylate in which an acid component is generated exhibits deteriorated water resistance in addition to the problems of odor and corrosion of apparatus, and thus the cured product absorbs moisture and peeling of the coated surface and a decrease in adhesive strength are caused in some cases in the case of using the (meth)acrylate in the coating agent and adhesive applications. In addition, the (meth)acrylate is exposed to a heating and stirring treatment for homogenization at the time of blending and a heat resistance test after curing in some cases. However, (meth)acrylic acid esters having poor thermal stability cannot be used at all in the optical lens application and the like which are required to exhibit transparency since coloration of the (meth)acrylic acid esters is caused in addition to the generation of a polymer and an acid component described above.

Patent Literature 1 discloses a method in which the reaction liquid after an esterification reaction using sulfonic acid as a catalyst is subjected to a neutralization treatment and a washing treatment, a quaternary ammonium salt or a quaternary phosphonium salt is further added to the resultant, and a heat treatment is conducted, but the operation is slightly complicated. In addition, Patent Literature 2 discloses a method in which a solvent and the like are added to the resultant after completion of a transesterification reaction using an organotin compound as a catalyst and precipitation and filtration are conducted, but the effect is insufficient and the purified product still contains several hundred ppm of tin.

CITATION LIST

Patent Literature

Patent Literature 1: JP 4811109 B2
Patent Literature 2: JP 2006-16322 A
Patent Literature 3: JP 4656351 B2

SUMMARY OF INVENTION

Technical Problem

The present invention has been made in view of the situation described above, and an object thereof is to obtain a high-quality (meth)acrylate from which a catalyst has been sufficiently removed by removing the catalyst used in the production of the (meth)acrylate through a simple operation.

Solution to Problem

The present inventors have conducted intensive investigations to solve the above problems. As a result, it has been found out that it is possible to obtain a high-quality (meth)acrylate from which the catalyst has been sufficiently removed by subjecting the reaction product of a transesterification reaction to a contact treatment with the following adsorbent C when a (meth)acrylate is produced by subjecting an alcohol and a monofunctional (meth)acrylate to a transesterification reaction using the following catalyst A and the following catalyst B concurrently, thereby completing the present invention.

Catalyst A: one or more kinds of compounds selected from the group consisting of a cyclic tertiary amine having an azabicyclo structure or a salt thereof or a complex thereof, an amidine or a salt thereof or a complex thereof, a compound having a pyridine ring or a salt thereof or a complex thereof, phosphines or a salt thereof or a complex thereof, and a compound having a tertiary diamine structure or a salt thereof or a complex thereof.

Catalyst B: one or more kinds of compounds selected from the group consisting of a compound containing zinc.

Adsorbent C: one or more kinds of compounds selected from the group consisting of an oxide and a hydroxide which contain at least one kind among magnesium, aluminum, and silicon.

Advantageous Effects of Invention

According to the production method of the present invention, it is possible to obtain a high-quality (meth)acrylate. It is possible to suitably use the (meth)acrylate obtained by the production method of the present invention in various kinds of industrial applications as a crosslinking component of blended materials such as paints, inks, adhesives, optical lenses, fillers, and molding materials or a reactive diluent component.

BRIEF DESCRIPTION OF DRAWINGS

The FIGURE is a schematic diagram illustrating the reaction mechanism in the method for producing a (meth) acrylate according to the present invention.

DESCRIPTION OF EMBODIMENTS

The present invention is to obtain a high-quality (meth)acrylate from which the catalyst has been sufficiently removed by subjecting the reaction product of a transesterification reaction to a contact treatment with the following adsorbent C when a (meth)acrylate is produced by subjecting an alcohol and a monofunctional (meth)acrylate to a transesterification reaction using the following catalyst A and the following catalyst B concurrently.

Catalyst A: one or more kinds of compounds selected from the group consisting of a cyclic tertiary amine having an azabicyclo structure or a salt thereof or a complex thereof, an amidine or a salt thereof or a complex thereof, a compound having a pyridine ring or a salt thereof or a complex thereof, phosphines or a salt thereof or a complex thereof, and a compound having a tertiary diamine structure or a salt thereof or a complex thereof.

Catalyst B: one or more kinds of compounds selected from the group consisting of a compound containing zinc.

Adsorbent C: one or more kinds of compounds selected from the group consisting of an oxide and a hydroxide which contain at least one kind among magnesium, aluminum, and silicon.

Incidentally, in the present invention, the "(meth)acrylate" means the target (meth)acrylate contained in the reaction product obtained in the present invention. The resulting (meth)acrylate is monofunctional, bifunctional, or polyfunctional depending on the number of hydroxyl groups in the alcohol to be used. In the present invention, the "monofunctional (meth)acrylate" means a (meth)acrylate to be used as a raw material.

Hereinafter, the present invention will be described in detail.

The alcohol to be used as a raw material in the present invention is an aliphatic alcohol, an alicyclic alcohol, an aromatic alcohol, a polyhydric alcohol ether, and the like which have at least one or more alcoholic hydroxyl groups in the molecule. The alcohol may have other functional groups or bonds, for example, a phenolic hydroxyl group, a ketone group, an acyl group, an aldehyde group, a thiol group, an amino group, an imino group, a cyano group, a nitro group, an ether bond, an ester bond, a carbonate bond, an amide bond, an imide bond, a peptide bond, a urethane bond, an acetal bond, a hemiacetal bond, and a hemiketal bond in the molecule.

Specific examples of the monohydric alcohol having one alcoholic hydroxyl group may include a monohydric alcohol having an ether bond in the molecule such as ethylene glycol monomethyl ether, diethylene glycol monomethyl ether, diethylene glycol monoethyl ether, triethylene glycol monomethyl ether, tetraethylene glycol monomethyl ether, polyethylene glycol monomethyl ether, dipropylene glycol monomethyl ether, tripropylene glycol monobutyl ether, polypropylene glycol monoethylether, 1,6-hexanediol monomethylether, 1,6-hexanediol monoethyl ether, tetramethylene glycol monomethyl ether, tetramethylene glycol monoethyl ether, polytetramethylene glycol monomethyl ether, polytetramethylene glycol monoethyl ether, glycidol, 2-(2-chloroethoxy)ethanol, 2-(2-dimethylaminoethoxy) ethanol, or an alkylene oxide modified product of 2-ethylhexyl alcohol; a monohydric alcohol having a vinyl group and an ether bond in the molecule such as 2-hydroxyethyl vinyl ether (another name: ethylene glycol monovinyl ether), 3-hydroxypropyl vinyl ether, 2-hydroxypropyl vinyl ether, 2-hydroxyisopropyl vinyl ether, 4-hydroxybutyl vinyl ether, 3-hydroxybutyl vinyl ether, 2-hydroxybutyl vinyl ether, 3-hydroxyisobutyl vinyl ether, 2-hydroxyisobutyl vinyl ether, 1-methyl-3-hydroxypropyl vinyl ether, 1-methyl-2-hydroxypropyl vinyl ether, 1-hydroxymethylpropyl vinyl ether, 4-hydroxycyclohexyl vinyl ether, 1,6-hexanediol monovinyl ether, tetramethylene glycol monovinyl ether, polytetramethylene glycol monovinyl ether 1,4-cyclohexanedimethanol monovinyl ether, 1,3-cyclohexanedimethanol monovinyl ether, 1,2-cyclohexanedimethanol monovinyl ether, isosorbide monovinyl ether, p-xylene glycol monovinyl ether, m-xylene glycol monovinyl ether, o-xylene glycol monovinyl ether, diethylene glycol monovinyl ether, triethylene glycol monovinyl ether, tetraethylene glycol monovinyl ether, pentaethylene glycol monovinyl ether, oligoethylene glycol monovinyl ether, polyethylene glycol monovinyl ether, dipropylene glycol monovinyl ether, tripropylene glycol monovinyl ether, tetrapropylene glycol monovinyl ether, pentapropylene glycol monovinyl ether, oligopropylene glycol monovinyl ether, polypropylene glycol monovinyl ether, or ethylene glycol-propylene glycol copolymer monovinyl ether; a monohydric alcohol having a ring structure such as tricyclo[5.2.1.0$^{2,6}$]decenol (another name: hydroxydicyclopentadiene), tricyclo[5.2.1.0$^{2,6}$]decanol, tricyclo[5.2.1.0$^{2,6}$]decenyloxyethanol, tricyclo[5.2.1.0$^{2,6}$]decanyloxyethanol, tricyclo[5.2.1.0$^{2,6}$]decenyloxypropanol, tricyclo[5.2.1.0$^{2,6}$]decanyloxypropanol, tricyclo[5.2.1.0$^{2,6}$]decenyloxyethoxyethanol, tricyclo[5.2.1.0$^{2,6}$]decanyloxyethoxyethanol, 4-hydroxy-2,2,6,6-tetramethylpiperidine, 4-hydroxy-1,2,2,6,6-pentamethylpiperidine, oxetanylmethanol, tetrahydrofurfuryl alcohol, tetrahydropyranyl alcohol, 1,4-cyclohexanedimethanol monomethyl ether, 1,3-cyclohexanedimethanol monomethyl ether, 1,2-cyclohexanedimethanol monomethyl ether, isosorbide monomethyl ether, isosorbide monoethyl ether, 2,3-O-sec-butylidene glycerol, 5-ethyl-5-(hydroxylmethyl)-1,3-dioxane, α-hydroxy-γ-butyrolactone, glycerol 1,2-carbonate, 1,3-dioxolan-4-ylmethanol, 2,2-dimethyl-1,3-dioxolane-4-methanol, β-hydroxy-γ-butyrolactone, α-hydroxymethyl-γ-butyrolactone, or β-hydroxymethyl-γ-butyrolactone; and an alcohol having an aromatic ring such as benzyl alcohol, phenoxyethanol, phenoxypropanol, p-xylene glycol monomethyl ether, m-xylene glycol monomethyl ether, o-xylene glycol monomethyl ether, an alkylene oxide modified product of phenol, an alkylene oxide modified product of o-phenylphenol, an alkylene oxide modified product of p-cumylphenol, or an alkylene oxide modified product of nonylphenol.

Specific examples of the dihydric alcohol having two alcoholic hydroxyl groups may include ethylene glycol, diethylene glycol, triethylene glycol, polyethylene glycol, propylene glycol, trimethylene glycol, dipropylene glycol, tripropylene glycol, polypropylene glycol, butanediol, pentanediol, hexanediol, heptanediol, nonanediol, neopentyl glycol, cyclohexanediol, cyclohexanedimethanol, dioxane glycol, N-methyldiethanolamine, N-ethyldiethanolamine, N-butyldiethanolamine, N-tert-butyldiethanolamine, N-lauryldiethanolamine, stearyldiethanolamine, N-phenyldiethanolamine, m-tolyldiethanolamine, p-tolyldiethanolamine, N,N'-bis(2-hydroxypropyl) aniline, N-nitrosodiethanolamine, N-(2-hydroxyethyl) lactamide, N,N'-bis(2-hydroxyethyl)oxamide, 3-morpholino-1,2-propanediol, 2,6-pyridinedimethanol, 3-(dimethylamino)-1,2-propanediol, 3-(diethylamino)-1,2-propanediol, alloxanthine dihydrate, (+)-N,N,N',N'-tetramethyl-L-tartaric acid diamide, (−)-N,N,N',N'-tetramethyl-D-tartaric acid diamide, N-propyl-N-(2,3-dihydroxypropyl)perfluoro-n-octylsulfonamide, thymidine, chloramphenicol, thiamphenicol, D-erythronolactone, methyl 4,6-O-benzylidene-α-D-glucopyranoside, phenyl 4,6-O-benzylidene-1-thio-β-D-glucopyranoside, 1,2:5,6-di-O-isopropylidene-D-mannitol, 1,2-O-isopropylidene-α-D-xylofuranose, 2,6-di-O-palmitoyl-L-ascorbic acid, isosorbide, and alkylene oxide adducts thereof, and further alkylene oxide adducts of compounds having a phenolic hydroxyl group such as hydroquinone, bisphenol A, bisphenol AP, bisphenol AF, bisphenol B, bisphenol BP, bisphenol C, bisphenol E, bisphenol F, bisphenol G, bisphenol M, bisphenol S, thiobisphenol, bisphenol P, bisphenol PH, bisphenol TMC, and bisphenol Z, and alcohols having a carbonate bond such as polycarbonatediol.

Specific examples of the trihydric alcohol having three alcoholic hydroxyl groups may include trimethylolethane, trimethylolpropane, glycerin, tris(2-hydroxyethyl) isocyanurate, hexanetriol, octanetriol, decanetriol, triethanolamine, triisopropanolamine, 1-[bis(2-hydroxyethyl)amino]-2-propanol, D-panthenol, DL-panthenol, uridine, 5-methyluridine, cytidine, inosine, adenosine, leucomycin A3, leucomycin A4, leucomycin A6, leucomycin A8, clindamycin hydrochloride monohydrate, prednisolone, methyl β-D-arabinopyranoside, methyl β-L-fucopyranoside, methyl α-L-fucopyranoside, D-galactar, 4-methoxyphenyl 3-O-allyl-β-D-galactopyranoside, 4-methoxyphenyl 3-O-benzyl-β-D-galactopyranoside, 1,6-anhydro-β-D-glucose, α-chloralose, β-chloralose 4,6-O-ethylidene-α-D-glucopyranose, D-glucal, 1,2-O-isopropylidene-α-D-glucofuranose, D-glucurono-6,3-lactone, 2-deoxy-D-ribose, methyl β-D-ribofuranoside, D-(+)-ribono-1,4-lactone, methyl-β-D-xylopyranoside, 6-O-palmitoyl-L-ascorbic acid, 6-O-stearoyl-L-ascorbic acid, 3-O-ethyl-L-ascorbic acid, and alkylene oxide adducts thereof.

Specific examples of the tetrahydric alcohol having four alcoholic hydroxyl groups may include ditrimethylolethane, ditrimethylolpropane, diglycerin, pentaerythritol, N,N,N',N'-tetrakis(2-hydroxyethyl)butanediamide, N,N,N',N'-tetrakis(2-hydroxypropyl)butanediamide, N,N,N',N'-tetrakis(2-hydroxyethyl)hexanediamide, N,N,N',N'-tetrakis(2-hydroxypropyl)hexanediamide, N,N,N',N'-tetrakis(2-hydroxyethyl)ethylenediamine, N,N,N',N'-tetrakis(2-hydroxypropyl)ethylenediamine, N-hexanoyl-D-glucosamine, N-valeryl-D-glucosamine, N-trifluoroacetyl-D-glucosamine, N-benzoyl-D-glucosamine, 5-acetamido-N,N'-bis(2,3-dihydroxypropyl)-2,4,6-triiodoisophthalamide, spiramycin, clarithromycin, leucomycin A1, leucomycin A5, leucomycin A7, leucomycin A9, leucomycin A13, lincomycin hydrochloride monohydrate, diazolidinyl urea, D-(−)-arabinose, DL-arabinose, L-(+)-arabinose, meso-erythritol, D-(+)-fucose, L-(−)-fucose, allyl α-D-galactopyranoside, methyl β-D-galactopyranoside, methyl α-D-galactopyranoside monohydrate, 4-methoxyphenyl β-D-galactopyranoside, 2-nitrophenyl β-D-galactopyranoside, 4-nitrophenyl α-D-galactopyranoside, 4-nitrophenyl β-D-galactopyranoside, phenyl β-D-galactopyranoside, N-acetyl-D-galactosamine hydrate, D-(+)-galactosamine hydrochloride, arbutin, 2-deoxy-D-glucose, esculin 1.5 hydrate, D-(+)-glucono-1,5-lactone, D-glucuronamide, helicin, methyl α-D-glucopyranoside, methyl β-D-glucopyranoside 0.5 hydrate, 4-methoxyphenyl β-D-glucopyranoside, 4-nitrophenyl β-D-glucopyranoside monohydrate, 4-nitrophenyl α-D-glucopyranoside, nonyl β-D-glucopyranoside, n-octyl β-D-glucopyranoside, phenyl β-D-glucopyranoside hydrate, phlorizin hydrate, Piceid, puerarin, N-acetyl-D-glucosamine, N-benzoyl-D-glucosamine, D-(+)-glucosamine hydrochloride, N-hexanoyl-D-glucosamine, N-valeryl-D-glucosamine, L-(+)-gulonic acid γ-lactone, D-(−)-lyxose, L-(+)-lyxose, 3,4-O-isopropylidene-D-mannitol, methyl α-D-mannopyranoside, D-mannono-1,4-lactone, 4-methoxyphenyl α-D-mannopyranoside, N-acetyl-D-mannosamine monohydrate, D-(−)-ribose, L-ribose, D-(+)-xylose, DL-xylose, L-(−)-xylose, D-araboascorbic acid, L-ascorbic acid, L-threitol, and alkylene oxide adducts thereof.

Specific examples of the pentahydric alcohol having five alcoholic hydroxyl groups may include tritrimethylolethane, tritrimethylolpropane, triglycerol, bis(2-hydroxyethyl)aminotris(hydroxymethyl) methane, bis(2-hydroxypropyl)aminotris(hydroxymethyl) methane, N,N,N',N'',N''-pentakis(2-hydroxyethyl)diethylenetriamine, N,N,N',N'',N''-pentakis(2-hydroxypropyl)diethylenetriamine, miglitol, erythromycin, azithromycindihydrate, D-(+)-arabitol, DL-arabitol, L-(−)-arabitol, D-(−)-fructose, L-(+)-fructose, D-(+)-galactose, L-(−)-galactose, β-D-glucose, D-(+)-glucose, L-(−)-glucose, D-glucose diethylmercaptal, salicin, L-gulose, D-(+)-mannose, L-(−)-mannose, ribitol, L-(−)-sorbose, D-tagatose, xylitol, sucralose, glyceryl ascorbate, and alkylene oxide adducts thereof.

Specific examples of the polyhydric alcohol having six or more alcoholic hydroxyl groups may include polytrimethylolethane, polytrimethylolpropane, polyglycerin, dipentaerythritol, tripentaerythritol, polypentaerythritol, iohexol, galactitol, D-sorbitol, L-sorbitol, myo-inositol, scyllo-inositol, D-mannitol, L-mannitol, icariin, amygdalin, D-(+)-cellobiose, diosmine, 2-O-α-D-glucopyranosyl-L-ascorbic acid, hesperidin, D-(+)-lactosemonohydrate, lactulose, D-(+)-maltosemonohydrate, D-(+)-melibiose monohydrate, methyl hesperidin, maltitol, naringin hydrate, neohesperidin dihydrochalcone hydrate, palatinose hydrate, rutin hydrate, D-(+)-sucrose, stevioside, D-(+)-turanose, D-(+)-trehalose (anhydrous), D-(+)-trehalose dihydrate, D-(+)-melezitose hydrate, D-(+)-raffinose pentahydrate, rebaudioside A, stachyose, α-cyclodextrin, β-cyclodextrin, γ-cyclodextrin, starch, polyvinyl alcohol, and alkylene oxide adducts thereof.

In the present invention, these alcohols can be used singly or in arbitrary combination of two or more kinds thereof. Among these alcohols, polyhydric alcohols having three or more alcoholic hydroxyl groups are preferable, and particularly, trimethylolethane, trimethylolpropane, glycerin, an alkylene oxide adduct of glycerin, tris(2-hydroxyethyl) isocyanurate, triethanolamine, ditrimethylolethane, ditrimethylolpropane, diglycerin, an alkylene oxide adduct of diglycerin, pentaerythritol, an alkylene oxide adduct of pentaerythritol, xylitol, dipentaerythritol, an alkylene oxide adduct of dipentaerythritol, D-sorbitol, and polyglycerin are preferable. Incidentally, in a case in which there are hydrates or solvates of these alcohols, the hydrates and solvates thereof can also be used as an alcohol in the production method of the present invention.

In the present invention, the monofunctional (meth)acrylate to be used as a raw material is a compound having one (meth)acryloyl group in the molecule, and examples thereof may include a compound represented by the following general formula (1).

[Chemical formula 1]

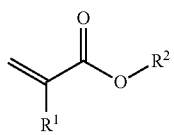

(1)

In the formula, $R^1$ represents a hydrogen atom or a methyl group. $R^2$ represents an organic group having from 1 to 50 carbon atoms.

Specific examples of $R^2$ in the general formula (1) may include a methyl group, an ethyl group, a n- or i-propyl group, a n-, i-, or t-butyl group, a n-, s-, or t-amyl group, a neopentyl group, a n-, s-, or t-hexyl group, a n-, s-, or t-heptyl group, a n-, s-, or t-octyl group, a 2-ethylhexyl group, a capryl group, a nonyl group, a decyl group, a undecyl group, a lauryl group, a tridecyl group, a myristyl group, a pentadecyl group, a cetyl group, a heptadecyl group, a stearyl group, a nonadecyl group, an aralkyl group, a seryl group, a myricyl group, a melissyl group, a vinyl group, an allyl group, a methallyl group, a crotyl group, a 1,1-dimethyl-2-propenyl group, a 2-methylbutenyl group, a 3-methyl-2-butenyl group, a 3-methyl-3-butenyl group, a 2-methyl-3-butenyl group, a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an oleyl group, a linole group, a linolen group, a cyclopentyl group, a cyclopentylmethyl group, a cyclohexyl group, a cyclohexylmethyl group, a 4-methylcyclohexyl group, a 4-t-butylcyclohexyl group, a tricyclodecanyl group, an isobornyl group, an adamantyl group, a dicyclopentenyl group, a dicyclopentenyl group, a phenyl group, a methylphenyl group, a dimethylphenyl group, a trimethylphenyl group, a 4-t-butylphenyl group, a benzyl group, a diphenylmethyl group, a diphenylethyl group, a triphenylmethyl group, a cinnamyl group, a naphthyl group, an anthranyl group, a methoxyethyl group, a methoxyethoxyethyl group, a methoxyethoxyethoxyethyl group, a 3-methoxybutyl group, an ethoxyethyl group, an ethoxyethoxyethyl group, a cyclopentoxyethyl group, a cyclohexyloxyethyl group, a cyclopentoxyethoxyethyl group, a cyclohexyloxyethoxyethyl group, a dicyclopentenyloxyethyl group, a phenoxyethyl group, a phenoxyethoxyethyl group, a glycidyl group, a β-methylglycidyl group, a β-ethylglycidyl group, a 3,4-epoxycyclohexylmethyl group, a 2-oxetanemethyl group, a 3-methyl-3-oxetanemethyl group, a 3-ethyl-3-oxetanemethyl group, a tetrahydrofuranyl group, a tetrahydrofurfuryl group, a tetrahydropyranyl group, a dioxazolanyl group, a dioxanyl group, a N,N-dimethylaminoethyl group, a N,N-diethylaminoethyl group, a N,N-dimethylaminopropyl group, a N,N-diethylaminopropyl group, a N-benzyl-N-methylaminoethyl group, and a N-benzyl-N-methylaminopropyl group.

In the present invention, these monofunctional (meth)acrylates can be used singly or in arbitrary combination of two or more kinds thereof. Among these monofunctional (meth)acrylates, methyl acrylate, ethyl acrylate, n-butyl acrylate, i-butyl acrylate, 2-ethylhexyl acrylate, 2-methoxyethyl acrylate, and 2-dimethylaminoethyl acrylate are preferable. In particular, methyl acrylate, ethyl acrylate, n-butyl acrylate, i-butyl acrylate, and 2-methoxyethyl acrylate which exhibit favorable reactivity to most alcohols and are easily available are preferable. Furthermore, 2-methoxyethyl acrylate which promotes the dissolution of alcohol and exhibits significantly favorable reactivity is more preferable.

The proportion of the monofunctional (meth)acrylate used to the alcohol used in the production method of the present invention is not particularly limited, but the monofunctional (meth)acrylate is used preferably at from 0.4 to 10.0 moles and more preferably at from 0.6 to 5.0 moles with respect to 1 mole of hydroxyl group in the alcohol. Side reactions increase when the amount of the monofunctional (meth)acrylate used is less than 0.4 mole. In addition, the amount of target (meth)acrylate generated is small and the productivity deteriorates when the amount of the monofunctional (meth)acrylate used is more than 10.0 moles.

The production method of the present invention can be carried out without using a solvent, but a solvent may be used if necessary. Specific examples of the solvent may include a hydrocarbon such as n-hexane, cyclohexane, methylcyclohexane, n-heptane, n-octane, n-nonane, n-decane, benzene, toluene, xylene, ethylbenzene, diethylbenzene, isopropylbenzene, amylbenzene, diamylbenzene, triamylbenzene, dodecylbenzene, didodecylbenzene, amyltoluene, isopropyltoluene, decalin, or tetralin; an ether such as diethyl ether, dipropyl ether, diisopropyl ether, dibutyl ether, diamyl ether, diethyl acetal, dihexyl acetal, t-butyl methyl ether, cyclopentyl methyl ether, tetrahydrofuran, tetrahydropyran, trioxane, dioxane, anisole, diphenyl ether, dimethyl cellosolve, diglyme, triglyme, ortetraglyme; a crown ether such as 18-crown-6; an alcohol such as methanol, ethanol, n-propanol, i-propanol, n-butanol, i-butanol, t-butanol, ethylene glycol, 2-methoxyethanol, or glycerin; an ester such as methyl benzoate and γ-butyrolactone; a ketone such as acetone, methyl ethyl ketone, methyl isobutyl ketone, cyclohexanone, acetophenone, or benzophenone; a sulfone such as sulfolane; a sulfoxide such as dimethylsulfoxide; a carbonate compound such as dimethyl carbonate, diethyl carbonate, ethylene carbonate, propylene carbonate, or 1,2-butylene carbonate; a urea or a derivative thereof; a phosphines oxide such as tributylphosphine oxide; an ionic liquid such as an imidazolium salt, a piperidinium salt, or a pyridinium salt; silicone oil, and water. Among these solvents, a hydrocarbon, an ether, an alcohol, a carbonate compound, and an ionic liquid are preferable. These solvents may be used singly, or two or more kinds thereof may be arbitrarily combined and used as a mixed solvent.

The catalyst A in the production method of the present invention is one or more kinds of compounds selected from the group consisting of a cyclic tertiary amine having an azabicyclo structure or a salt thereof or a complex thereof, an amidine or a salt thereof or a complex thereof, a compound having a pyridine ring or a salt thereof or a complex thereof, phosphines or a salt thereof or a complex thereof, and a compound having a tertiary diamine structure or a salt thereof or a complex thereof.

Specific examples of the cyclic tertiary amine having an azabicyclo structure or a salt thereof or a complex thereof may include 1-azabicyclo[1,1,0]butane, 1,3-diazabicyclo[1,1,0]butane, 1-azabicyclo[2,1,0]heptane, 1,3-diazabicyclo[2,1,0]heptane, 1,4-diazabicyclo[2,1,0]heptane, 1-azabicyclo[2,2,0]hexane, 1,3-diazabicyclo[2,2,0]hexane, 1-azabicyclo[2,1,1]hexane, 1,3-diazabicyclo[2,1,1]hexane, 1-azabicyclo[2,2,1]heptane, 1,3-diazabicyclo[2,2,1]heptane, 1,4-diazabicyclo[2,2,1]heptane, 1-azabicyclo[3,2,0]heptane, 1,3-diazabicyclo[3,2,0]heptane, 1,4-diazabicyclo[3,2,0]heptane, 1,6-diazabicyclo[3,2,0]heptane, 1,3-diazabicyclo[2,2,2]octane, 1-azabicyclo[3,2,1]octane, 1,3-diazabicyclo[3,2,1]octane, 1,4-diazabicyclo[3,2,1]octane, 1,5-diazabicyclo[3,2,1]octane, 1,6-diazabicyclo[3,2,1]octane, 1-azabicyclo[4,1,1]octane, 1,3-diazabicyclo[4,1,1]octane, 1,4-diazabicyclo[4,1,1]octane, 1,5-diazabicyclo[4,1,1]octane, 1,6-diazabicyclo[4,1,1]octane, 1,7-diazabicyclo[4,1,1]octane, 1-azabicyclo[4,2,0]octane, 1,3-diazabicyclo[4,2,0]octane, 1,4-diazabicyclo[4,2,0]octane, 1,5-diazabicyclo[4,2,0]octane, 1,7-diazabicyclo[4,2,0]octane, 1-azabicyclo[3,3,1]nonane, 1,3-diazabicyclo[3,3,1]nonane, 1,4-diazabicyclo[3,3,1]nonane, 1,5-diazabicyclo[3,3,1]nonane, 1-azabicyclo[3,2,2]nonane, 1,3-diazabicyclo[3,2,2]nonane, 1,4-diazabicyclo[3,2,2]nonane, 1,5-diazabicyclo[3,2,2]nonane, 1,6-diazabicyclo[3,2,2]nonane, 1,8-diazabicyclo[3,2,2]nonane, 1-azabicyclo[4,3,0]nonane, 1,3-diazabicyclo[4,3,0]nonane, 1,4-diazabicyclo[4,3,0]nonane, 1,5-diazabicyclo[4,3,0]nonane, 1,6-diazabicyclo[4,3,0]nonane, 1,7-diazabicyclo[4,3,0]nonane, 1,8-diazabicyclo[4,3,0]nonane, 1-azabicyclo[4,2,1]nonane, 1,3-diazabicyclo[4,2,1]nonane, 1,4-diazabicyclo[4,2,1]nonane, 1,5-diazabicyclo[4,2,1]nonane, 1,6-diazabicyclo[4,2,1]nonane, 1,7-diazabicyclo[4,2,1]nonane, 1-azabicyclo[5,2,0]nonane, 1,3-diazabicyclo[5,2,0]nonane, 1,4-diazabicyclo[5,2,0]nonane, 1,5-diazabicyclo[5,2,0]nonane, 1,6-diazabicyclo[5,2,0]nonane, 1,7-diazabicyclo[5,2,0]nonane, 1,8-diazabicyclo[5,2,0]nonane, 1-azabicyclo[5,1,1]nonane, 1,3-diazabicyclo[5,1,1]nonane, 1,4-diazabicyclo[5,1,1]nonane, 1,5-diazabicyclo[5,1,1]nonane, 1,6-diazabicyclo[5,1,1]nonane, 1,7-diazabicyclo[5,1,1]nonane, 1-azabicyclo[6,1,0]nonane, 1,3-diazabicyclo[6,1,0]nonane, 1,4-diazabicyclo[6,1,0]nonane, 1,5-diazabicyclo[6,1,0]nonane, 1,6-diazabicyclo[6,1,0]nonane, 1,7-diazabicyclo[6,1,0]nonane, 1,8-diazabicyclo[6,1,0]nonane, 1-azabicyclo[7,1,0]decane, 1,9-diazabicyclo[7,1,0]decane, 1-azabicyclo[6,2,0]decane, 1,8-diazabicyclo[6,2,0]decane, 1-azabicyclo[6,1,1]decane, 1,8-diazabicyclo[6,1,1]decane, 1-azabicyclo[5,3,0]decane, 1,7-diazabicyclo[5,3,0]decane, 1-azabicyclo[5,2,1]decane, 1,7-diazabicyclo[5,2,1]decane, 1-azabicyclo[4,3,1]decane, 1,6-diazabicyclo[4,3,1]decane, 1-azabicyclo[4,2,2]decane, 1,6-diazabicyclo[4,2,2]decane, 1-azabicyclo[5,4,0]undecane, 1,7-diazabicyclo[5,4,0]undecane, 1-azabicyclo[5,3,1]undecane, 1,7-diazabicyclo[5,3,1]undecane, 1-azabicyclo[5,2,2]undecane, 1,7-diazabicyclo[5,2,2]undecane, 1-azabicyclo[4,4,1]undecane, 1,7-diazabicyclo[4,4,1]undecane, 1-azabicyclo[4,3,2]undecane, 1,7-diazabicyclo[4,3,2]undecane, 1-azabicyclo[3,3,0]octane, 1-azabicyclo[4,3,0]nonane, quinuclidine, lupinane, lupinine, quinolizidine, 3-hydroxyquinuclidine, 3-quinuclidinone, quincorine, quincoridine, cinchonidine, cinchonine, quinidine, quinine, cupreine, ibogaine, swainsonine, castanospermine, mianserin, mirtazapine, canadine, Troger's base, 1-azabicyclo[2,2,2]octane-3-carboxylic acid, triethylenediamine (another name: DABCO), 2-(hydroxymethyl)triethylenediamine, hexamethylenetetramine, 3-quinolizinone hydrochloride, 3-chloro-1-azabicyclo[2,2,2]octane hydrochloride, cinchonidine dihydrochloride, cinchonine hydrochloride hydrate, cinchonidine sulfate dihydrate, hydroquinidine hydrochloride, cinchonine sulfate dihydrate, quinine hydrochloride dihydrate, quinine sulfate dihydrate, quinine phosphate, quinidine sulfate dihydrate, mianserine hydrochloride, 1,1'-(butane-1,4-diyl)bis[4-aza-1-azoniabicyclo[2,2,2]octane]dibromide, 1,1'-(decane-1,10-diyl)bis[4-aza-1-azoniabicyclo[2,2,2]octan e]dibromide, bis(trimethylaluminum)-1,4-diazabicyclo[2,2,2]octane adduct, bismuthine, quinuclidine hydrochloride, 3-quinuclidinone hydrochloride, 3-hydroxyquinuclidine hydrochloride, DABCO hydrochloride, 2-(hydroxymethyl)triethylenediamine hydrochloride, quinuclidine acetate, 3-quinuclidinone acetate, 3-hydroxyquinuclidine acetate, DABCO acetate, 2-(hydroxymethyl)triethylenediamine acetate, quinuclidine acrylate, 3-quinuclidinone acrylate, 3-hydroxyquinuclidine acrylate, DABCO acrylate, and 2-(hydroxymethyl)triethylenediamine acrylate.

Specific examples of the amidine or a salt thereof or a complex thereof may include imidazole, N-methylimidazole, N-ethylimidazole, 1-benzyl-2-methylimidazole, 1-benzyl-2-phenylimidazole, 1-vinylimidazole, 1-allylimidazole, 1,8-diazabicyclo[5,4,0]undec-7-ene (another name: DBU), 1,5-diazabicyclo[4,3,0]non-5-ene (anothername: DBN), N-methylimidazole hydrochloride, DBU hydrochloride, DBN hydrochloride, N-methylimidazole acetate, DBU acetate, DBN acetate, N-methylimidazole acrylate, DBU acrylate, DBN acrylate, and phthalimide DBU.

Specific examples of the compound having a pyridine ring or a salt thereof or a complex thereof may include pyridine, 2-methylpyridine, 3-methylpyridine, 4-methylpyridine, 2-ethylpyridine, 3-ethylpyridine, 4-ethylpyridine, 2-propylpyridine, 4-propylpyridine, 4-isopropyl pyridine, 4-tert-butyl pyridine, 4-amylpyridine, 4-(1-ethylpropyl)pyridine, 4-(5-nonyl)pyridine, 2-vinylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 3,5-diethylpyridine, N,N-dimethyl-4-aminopyridine (another name: DMAP), 2,4,6-trimethylpyridine, 2,6-di-tert-butylpyridine, N,N-dimethyl-2-aminopyridine, 4-piperidinopyridine, 4-pyrrolidinopyridine, 4-phenylpyridine, quinoline, 2-methylquinoline, 3-methylquinoline, 4-methylquinoline, 6-methylquinoline, 7-methylquinoline, 8-methylquinoline, isoquinoline, 1-methylisoquinoline, acridine, 3,4-benzoquinoline, 5,6-benzoquinoline, 7,8-benzoquinoline, 2-hydroxypyridine, 3-hydroxypyridine, 4-hydroxypyridine, 2,6-dihydroxypyridine, 2-(hydroxymethyl)pyridine, 3-(hydroxymethyl)pyridine, 4-(hydroxymethyl)pyridine, 5-hydroxyisoquinoline, 2-methoxypyridine, 3-methoxypyridine, 4-methoxypyridine, 2,6-dimethoxypyridine, 1,5-naphthyridine, 1,6-naphthyridine, 1,7-naphthyridine, 1,8-naphthyridine, 2,6-naphthyridine, 2,7-naphthyridine, 2,2'-bipyridyl, 3,3'-bipyridyl, 4,4'-bipyridyl, 2,3'-bipyridyl, 2,4'-bipyridyl, 3,4'-bipyridyl, 4,4'-ethylenedipyridine, 1,3-di(4-pyridyl)propane, 1,10-phenanthroline monohydrate, 2-(trimethylsilyl)pyridine, DMAP hydrochloride, DMAP acetate, DMAP acrylate, 1-methylpyridinium chloride, 1-propylpyridinium chloride, borane-pyridine complex, borane-2-picoline complex, and pyridinium p-toluenesulfonate.

Examples of phosphines or a salt thereof or a complex thereof may include a compound containing a structure represented by the following general formula (2)

[Chemical Formula 2]

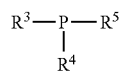

(2)

In the formula, $R^3$, $R^4$, and $R^5$ may be the same as or different from one another, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have a substituent.

Specific examples thereof may include triphenylphosphine, (S)-(−)-BINAP, (R)-(+)-BINAP, (±)-BINAP, 2,2'-bis(diphenylphosphino)biphenyl, xantphos, 4,6-bis(diphenylphosphino)phenoxazine, bis[2-(diphenylphosphino)phenyl]ether, (2-bromophenyl)diphenylphosphine, bis(pentafluorophenyl)phenylphosphine, sodium diphenylphosphinobenzene-3-sulfonate, diphenyl-1-pyrenylphosphine, diphenyl-2-pyridylphosphine, 4-(dimethylamino)phenyldiphenylphosphine, 1,1'-bis(diphenylphosphino)ferrocene, (R,R'')-2,2''-bis(diphenylphosphino)-1,1''-biferocene, (R)—N,N-dimethyl-1-[(S)-2-(diphenylphosphino)ferrocenyl]ethylamine, (S)—N,N-dimethyl-1-[(R)-2-(diphenylphosphino)ferrocenyl]ethylamine, (R)—N,N-dimethyl-1-[(S)-1',2-bis(diphenylphosphino)ferrocenyl]ethylamine, (S)—N,N-dimethyl-1-[(R)-1',2-bis(diphenylphosphino)ferrocenyl]ethylamine, 4-diphenylphosphinomethyl polystyrene resin, (R)-(+)-2-diphenylphosphino-2'-methoxy-1,1'-binaphthyl, (S)-(−)-2-diphenylphosphino-2'-methoxy-1,1'-binaphthyl, 2-(diphenylphosphino)benzoic acid, 4-(diphenylphosphino)benzoic acid, 2-(diphenylphosphino)benzaldehyde, (S)-(−)-5,5'-bis[di(3,5-xylyl)phosphino]-4,4'-bi-1,3-benzodioxole, (R)-(+)-5,5'-bis[di(3,5-xylyl)phosphino]-4,4'-bi-1,3-benzodioxole, (S)-(+)-5,5'-bis[di(3,5-di-tert-butyl-4-methoxyphenyl)phosphino]-4,4'-bi-1,3-benzodioxole, (R)-(−)-5,5'-bis[di(3,5-di-tert-butyl-4-methoxyphenyl)phosphino]-4,4'-bi-1,3-benzodioxole, (pentafluorophenyl)diphenylphosphine, (S)-(−)-5,5'-bis(diphenylphosphino)-4,4'-bi-1,3-benzodioxole, (R)-(+)-5,5'-bis(diphenylphosphino)-4,4'-bi-1,3-benzodioxole, tris(4-methoxyphenyl)phosphine, tri(p-tolyl)phosphine, tri(o-tolyl)phosphine, tri(m-tolyl)phosphine, tris(2,6-dimethoxyphenyl)phosphine, triphenylborane-triphenylphosphine complex, triphenylphosphine borane, tris(pentafluorophenyl)phosphine, tris[3,5-bis(trifluoromethyl)phenyl]phosphine, tris(4-fluorophenyl)phosphine, p-styryldiphenylphosphine, tetraphenylphosphonium bromide, methyltriphenylphosphonium bromide, n-butyltriphenylphosphonium bromide, methoxymethyltriphenylphosphonium chloride, benzyltriphenylphosphonium chloride, tetraphenylphosphonium tetraphenylborate, tetraphenylphosphonium tetra-p-tolylborate, ethyltriphenylphosphonium acetate-acetic acid complex, ethyltriphenylphosphonium iodide, tris(4-methoxy-3,5-dimethylphenyl)phosphine, (+)-DIOP, (−)-DIOP, 1,2-bis(diphenylphosphino)ethane, 1,3-bis(diphenylphosphino)propane, 1,2-bis(dimethylphosphino)ethane, 1,4-bis(diphenylphosphino)butane, 1,6-bis(diphenylphosphino)hexane, 1,5-bis(diphenylphosphino)pentane, bis(diphenylphosphino)methane, trans-1,2-bis(diphenylphosphino)ethylene, (S,S)-chiraphos, (R,R)-DIPAMP, (S,S)-DIPAMP, 1,2-bis[bis(pentafluorophenyl)phosphino]ethane, (2R,3R)-(−)-Norphos, (2S,3S)-(+)-Norphos, 2-butenyl(di-tert-butyl)phosphine, cyclohexyldiphenylphosphine, dicyclohexyl(1,1-diphenyl-1-propen-2-yl)phosphine, diethylphenylphosphine, dicyclohexylphenylphosphine, diphenylpropylphosphine, 2-(di-tert-butylphosphino)biphenyl, 2-(dicyclohexylphosphino)biphenyl, 2-(dicyclohexylphosphino)-2'-(dimethylamino)biphenyl, 1-[2-(di-tert-butylphosphino)phenyl]-3,5-diphenyl-1H-pyrazole, di-tert-butylphenylphosphine, (4-dimethylaminophenyl)di-tert-butylphosphine, di-tert-butyl(3-methyl-2-butenyl)phosphine, ethyldiphenylphosphine, isopropyldiphenylphosphine, methyldiphenylphosphine, tricyclohexylphosphine, tri(2-furyl)phosphine, tri(2-thienyl)phosphine, tri-tert-butylphosphine, and tricyclopentylphosphine.

Examples of the compound having a tertiary diamine structure or a salt thereof or a complex thereof may include by a compound having a structure represented by the following general formula (3).

[Chemical Formula 3]

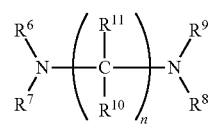

(3)

(In the formula, $R^4$, $R^7$, $R^8$, and $R^9$ are the same as or different from one another, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have an amino group, a hydroxyl group, an ether bond, an ester bond, a carbonate bond, an amide bond, or a urethane bond. $R^{10}$ and $R^{11}$ are a hydrogen atom or a methyl group. n is an integer from 1 to 12.)

Specific examples of the compound having a tertiary diamine structure or a salt thereof or a complex thereof may include N,N,N',N'-tetramethyldiaminomethane, N,N,N',N'-tetramethylethylenediamine, N,N,N',N'',N''-pentamethyldiethylenetriamine, tris[2-(dimethylamino)ethyl]amine, N,N,N',N'-tetramethyl-1,2-diaminopropane, N'-(2-hydroxyethyl)-N,N,N'-trimethylethylenediamine, 1-(2-dimethylaminoethyl)-4-methylpiperazine, N,N,N',N'-tetramethyl-1,3-propanediamine, N-methyl-N,N-bis[3-(dimethylamino)propyl]amine, N,N,N',N'-tetramethyl-2,2-dimethyl-1,3-propanediamine, N,N,N',N'-tetramethyl-1,3-butanediamine, N,N,N',N'-tetramethyl-1,4-butanediamine, N,N,N',N'-tetramethyl-1,6-hexanediamine, N,N,N',N'-tetramethyl-1,6-hexanediamine hydrochloride, N,N,N',N'-tetramethyl-1,6-hexanediamine acetate, and N,N,N',N'-tetramethyl-1,6-hexanediamine acrylate.

In the present invention, these catalysts A can be used singly or in arbitrary combination of two or more kinds thereof. Among these catalysts A, quinuclidine, 3-quinuclidinone, 3-hydroxyquinuclidine, DABCO, 2-(hydroxymethyl)triethylenediamine, N-methylimidazole, DBU, DBN, DMAP, triphenylphosphine, tri(p-tolyl)phosphine, tri(m-tolyl)phosphine, tris(4-methoxyphenyl)phosphine, tris(4-methoxy-3,5-dimethylphenyl)phosphine, and N,N,N',N'-tetramethyl-1,6-hexanediamine are preferable, and particularly, 3-hydroxyquinuclidine, DABCO, 2-(hydroxymethyl)triethylenediamine, N-methylimidazole, DBU, DMAP, triphenylphosphine, tri(m-tolyl)phosphine, and N,N,N',N'-tetramethyl-1,6-hexanediamine which exhibit favorable reactivity to most alcohols and are easily available are preferable.

The amount of the catalyst A used in the production method of the present invention is not particularly limited, but the catalyst A is used preferably at from 0.0001 to 0.5 mole and still more preferably at from 0.0005 to 0.2 mole with respect to 1 mole of hydroxyl group in the alcohol. The amount of target (meth)acrylate generated is small when the amount of the catalyst A used is less than 0.0001 mole, and the amount of by-products increases and the coloration of the reaction liquid increases so that the purification step after completion of the reaction is complicated when the amount of the catalyst A used is more than 0.5 mole.

The catalyst B in the production method of the present invention is one or more kinds of compounds selected from the group consisting of a compound containing zinc, and examples thereof may include a compound which contains a zinc salt of an organic acid and is represented by the following general formula (4), a compound which contains zinc diketone enolate and is represented by the following general formula (5), and zinc oxalate.

[Chemical Formula 4]

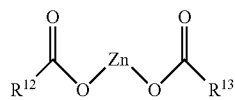

(4)

In the formula, $R^{12}$ and $R^{13}$ may be the same as or different from each other, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have a substituent. However, $R^{12}$ and $R^{13}$ do not have a halogen atom such as fluorine or chlorine.

[Chemical Formula 5]

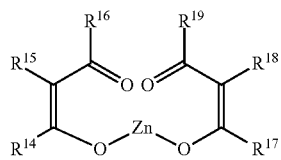

(5)

In the formula, $R^{14}$, $R^{15}$, $R^{16}$, $R^{17}$, $R^{18}$, and $R^{19}$ may be the same as or different from one another, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have a substituent, and further wherein $R^{15}$ and/or $R^{18}$ may be hydrogen atom.

Specific examples of the compound which contains zinc and is represented by the general formula (4) may include zinc acetate, zinc acetate dihydrate, zinc propionate, zinc octylate, zinc neodecanoate, zinc laurate, zinc myristate, zinc stearate, zinc cyclohexanebutyrate, zinc 2-ethylhexanoate, zinc benzoate, zinc t-butylbenzoate, zinc salicylate, zinc naphthenate, zinc acrylate, and zinc methacrylate. Incidentally, in a case in which there are hydrates, solvates, or complexes with the catalyst A of these compounds containing zinc, the hydrates, the solvates, and the complexes with the catalyst A can also be used as the catalyst B in the production method of the present invention.

Specific examples of the compound which contains zinc diketone enolate and is represented by the general formula (5) may include zinc acetylacetonate, zinc acetylacetonate hydrate, zinc bis(2,6-dimethyl-3,5-heptanedionato), zinc bis(2,2,6,6-tetramethyl-3,5-heptanedionato), and zinc bis(5,5-dimethyl-2,4-hexanedionato). Incidentally, in a case in which there are hydrates, solvates, or complexes with the catalyst A of these compounds containing zinc, the hydrates, the solvates, and the complexes with the catalyst A can also be used as the catalyst B in the production method of the present invention.

As the catalyst B in the production method of the present invention, the compounds described above can be directly used, but these compounds can also be generated in the reaction system and used. Examples thereof may include a method in which other zinc compounds such as metal zinc, zinc oxide, zinc hydroxide, zinc chloride, and zinc nitrate are used as a raw material and these zinc compounds are reacted with an organic acid in the case of a zinc salt of an organic acid and a method in which these zinc compounds are reacted with 1,3-diketone in the case of zinc diketone enolate.

In the production method of the present invention, these catalysts B can be used singly or in arbitrary combination of two or more kinds thereof. Among these catalysts B, zinc acetate, zinc propionate, zinc acrylate, zinc methacrylate, and zinc acetylacetonate are preferable. In particular, zinc acetate, zinc acrylate, and zinc acetylacetonate which exhibit favorable reactivity to most alcohols and are easily available are preferable.

The amount of the catalyst B used in the production method of the present invention is not particularly limited, but the catalyst B is used preferably at from 0.0001 to 0.5 mole and still more preferably at from 0.0005 to 0.2 mole with respect to 1 mole of hydroxyl group in the alcohol. The amount of the target (meth)acrylate generated is small when the amount of the catalyst B used is less than 0.0001 mole, and the amount of by-products increases and the color tone of the reaction liquid deteriorates so that the purification step after completion of the reaction is complicated when the amount of the catalyst B used is more than 0.5 mole.

The proportion of the catalyst A used to the catalyst B used in the production method of the present invention is not particularly limited, but the catalyst A is used preferably at from 0.005 to 10.0 moles and still more preferably at from 0.05 to 5.0 moles with respect to 1 mole of the catalyst B. The amount of the target (meth)acrylate generated is small when the proportion of the catalyst A used to the catalyst B used is less than 0.005 mole, and the amount of by-products increases and the color tone of the reaction liquid deteriorates so that the purification step after completion of the reaction is complicated when the proportion is more than 10.0 moles.

In the production method of the present invention, as the catalyst A and the catalyst B to be concurrently used, a combination in which the catalyst A is DABCO and the catalyst B is zinc acetate and/or zinc acrylate is the most preferable. This combination can be suitably used in various kinds of industrial applications in which the color tone is regarded as important since excellent color tone is exhibited after completion of the reaction as well as the target (meth)acrylate is obtained at a favorable yield by this combination. Furthermore, this combination is economically advantageous since it is a relatively inexpensively available catalyst.

In addition, it is possible to recover the catalyst A and/or the catalyst B from the reaction product after completion of the transesterification reaction of the production method of the present invention and to use the recovered catalysts in the transesterification reaction again.

In the production method of the present invention, it is presumed that the transesterification reaction proceeds by the reaction mechanism illustrated in the FIGURE. First, the electron density on the carbonyl oxygen atom increases as the catalyst A is added to the carbon at the β-position of the monofunctional (meth)acrylate, and the reaction intermediate illustrated in the FIGURE is generated as this further attacks the carbonyl carbon of another monofunctional (meth)acrylate. It is presumed that the target (meth)acrylate is generated as this intermediate undergoes the transesterification reaction with the alcohol thereafter. At this time, it is presumed that the catalyst B exhibiting Lewis acidity promotes the reaction mechanism illustrated in the FIGURE by activating the (meth)acryloyl group.

In the production method of the present invention, the catalyst A and the catalyst B to be used may be added from the beginning or the middle of the above reaction. In addition, the desired amount of the catalyst A and the catalyst B to be used may be added at once or dividedly. In addition, the catalyst A and/or the catalyst B may be added after being dissolved in a solvent in the case of a solid.

The reaction temperature for the transesterification reaction in the production method of the present invention is preferably from 40 to 180° C. and particularly preferably from 60 to 160° C. The reaction rate is significantly slow when the reaction temperature is lower than 40° C., and thermal polymerization of the (meth)acryloyl group takes place or the color tone of the reaction liquid deteriorates so that the purification step after completion of the reaction is complicated when the reaction temperature exceeds 180° C.

The reaction pressure for the transesterification reaction in the production method of the present invention is not particularly limited as long as it can maintain a predetermined reaction temperature, and the transesterification reaction may be conducted in a reduced pressure state or a pressurized state. The reaction pressure is usually from 0.000001 to 10 MPa (absolute pressure).

In the production method of the present invention, a monohydric alcohol derived from the monofunctional (meth)acrylate used as a raw material is generated as a by-product as the transesterification reaction proceeds. The monohydric alcohol may be allowed to coexist in the reaction system, but it is possible to further promote the advance of transesterification reaction by discharging the monohydric alcohol out of the reaction system.

In the production method of the present invention, an inert gas such as argon, helium, nitrogen, or carbon dioxide gas may be introduced into the system for the purpose of maintaining the color tone of the reaction liquid favorably. In addition, an oxygen-containing gas may be introduced into the system for the purpose of preventing polymerization of the (meth)acryloyl group. Specific examples of the oxygen-containing gas may include air, a mixed gas of oxygen with nitrogen, and a mixed gas of oxygen with helium. Examples of the method for introducing the gas may include a method in which the gas is blown (so-called bubbling) into the reaction product and a method in which the gas is introduced into the gas phase portion during the filtration operation such as pressure filtration or suction filtration.

In the production method of the present invention, it is preferable to add a polymerization inhibitor into the system for the purpose of preventing polymerization of the (meth)acryloyl group. Specific examples of the polymerization inhibitor may include an organic polymerization inhibitor such as hydroquinone, tert-butylhydroquinone, hydroquinone monomethyl ether, 2,6-di-tert-butyl-4-methylphenol, 2,4,6-tri-tert-butylphenol, 4-tert-butylcatechol, benzoquinone, phenothiazine, N-nitroso-N-phenylhydroxylamine ammonium, 2,2,6,6-tetramethylpiperidine-1-oxyl, or 4-hydroxy-2,2,6,6-tetramethylpiperidine-1-oxyl; an inorganic polymerization inhibitor such as copper chloride, copper sulfate, or iron sulfate; an organic salt-based polymerization inhibitor such as copper dibutyldithiocarbamate or N-nitroso-N-phenylhydroxylamine aluminum salt. The polymerization inhibitor may be added singly or in arbitrary combination of two or more kinds thereof. In addition, the polymerization inhibitor may be added from the beginning or the middle of the reaction. Furthermore, the desired amount of the polymerization inhibitor to be used may be added at once or dividedly. The polymerization inhibitor may be continuously added via the rectifying column. The amount of the polymerization inhibitor added is preferably from 5 to 30,000 ppm by mass and more preferably from 25 to 10,000 ppm by mass in the reaction liquid. The effect of inhibiting polymerization is insufficient when the amount of the polymerization inhibitor added is less than 5 ppm by mass, and the color tone of the reaction liquid deteriorates or the curing rate of the resulting (meth)acrylate decreases so that the purification step after completion of the reaction is complicated when the amount of the polymerization inhibitor added is more than 30,000 ppm by mass.

The reaction time for the transesterification reaction in the production method of the present invention varies depending on the kind and amount of catalyst used, the reaction temperature, the reaction pressure, and the like, but it is usually from 0.1 to 150 hours and preferably from 0.5 to 80 hours.

The transesterification reaction in the production method of the present invention can be conducted by any method of a batch method, a semi-batch method, or a continuous method. As an example of the batch method, an alcohol, a monofunctional (meth)acrylate, a catalyst, and a polymerization inhibitor are charged into a reactor and the mixture is stirred at a predetermined temperature while allowing an oxygen-containing gas to bubble in the reaction liquid. Thereafter, a monohydric alcohol derived from the monofunctional (meth)acrylate used as a raw material is generated as a by-product as the transesterification reaction proceeds. It is possible to generate the target (meth)acrylate by taking out the monohydric alcohol from the reactor at a predetermined pressure.

In the production method of the present invention, it is possible to obtain a high-quality (meth)acrylate from which the catalyst has been sufficiently removed by subjecting the reaction product of the transesterification reaction to a contact treatment with the adsorbent C.

The adsorbent C in the production method of the present invention is one or more kinds of compounds selected from the group consisting of an oxide and a hydroxide which contain at least one kind among magnesium, aluminum, and silicon.

Specific examples of the adsorbent C may include magnesium oxide (for example, KYOWAMAG (trade name) and KYOWAMAG MF (trade name) manufactured by Kyowa Chemical Industry Co., Ltd.), magnesium hydroxide (for example, KISUMA HB (trade name) manufactured by Kyowa Chemical Industry Co., Ltd.), aluminum oxide (for example, ACTIVATED ALUMINA AND HYDRAULIC ALUMINA manufactured by Sumitomo Chemical Co., Ltd., ACTIVATED ALUMINA GB (trade name) manufactured by MIZUSAWA INDUSTRIAL CHEMICALS, LTD., and KYOWAAD 200 (trade name) manufactured by Kyowa Chemical Industry Co., Ltd.), aluminum hydroxide and a hydrotalcite compound (for example, DHT-4A (trade name), KYOWAAD 500 (trade name), and KYOWAAD 1000 (trade name) manufactured by Kyowa Chemical Industry Co., Ltd.), magnesium-aluminum composite oxide (for example, KYOWAAD 300 (trade name) and KYOWAAD 2000 (trade name) manufactured by Kyowa Chemical Industry Co., Ltd.), magnesium silicate (for example, KYO-WAAD 600 (trade name) manufactured by Kyowa Chemical Industry Co., Ltd. and MIZUKALIFE (trade name) manufactured by MIZUSAWA INDUSTRIAL CHEMICALS, LTD.), aluminum silicate (for example, KYOWAAD 700 (trade name) manufactured by Kyowa Chemical Industry Co., Ltd. and NEOBEAD SA (trade name) manufactured by MIZUSAWA INDUSTRIAL CHEMICALS, LTD.), a montmorillonite-based compound (for example, GALLEON EARTH, (trade name), MIZUKAACE (trade name), and GALEONITE (trade name) manufactured by MIZUSAWA INDUSTRIAL CHEMICALS, LTD.), a bentonite-based compound (for example, BENCLAY (trade name) manufactured by MIZUSAWA INDUSTRIAL CHEMICALS, LTD.), a sepiolite-based compound (for example, ADEPLUS (trade name) manufactured by MIZUSAWA INDUSTRIAL CHEMICALS, LTD.), a silica-based compound (for example, SILHONITE (trade name) and SILBEAD N (trade name) manufactured by MIZUSAWA INDUSTRIAL CHEMICALS, LTD. and CARPLEX (trade name) manufactured by DSL. Japan), and zeolite (for example, MIZUKASIEVES (trade name) and MIZUKASIEVES EX (trade name) manufactured by MIZUSAWA INDUSTRIAL CHEMICALS, LTD.). These may be mined from nature or synthetic products. In addition, these may contain an alkali metal such as lithium, sodium, potassium, or cesium; an alkaline earth metal such as calcium; a transition element such as iron or zinc; a rare earth element such as cerium; water, a carbonate ion, and the like.

In the present invention, these adsorbents C can be used singly or in arbitrary combination of two or more kinds thereof. Among these adsorbents C, magnesium silicate, aluminum silicate, and a hydrotalcite compound are preferable, and particularly magnesium silicate and aluminum silicate which have extremely high adsorption capacity and are easily available are preferable.

The amount of the adsorbent C used in the production method of the present invention is not particularly limited, but the adsorbent C is used preferably at from 0.001 to 1.5 parts and particularly preferably at from 0.005 to 0.8 parts with respect to 1 part of the target (meth)acrylate. The effect of removing the catalyst is insufficient when the amount of the adsorbent C used is less than 0.001 parts, and separation of the adsorbent C from the target (meth)acrylate is complicated when the amount of the adsorbent C used is more than 1.5 parts.

The adsorbent C used in the production method of the present invention may be used from the beginning or the middle of the transesterification reaction, but it is preferably used after completion of the transesterification reaction. In addition, the desired amount of the adsorbent C to be used may be used at once or dividedly. The adsorbent C may be added after being dissolved in a solvent in the case of a solid, or it may be added after being wet with a solvent or as a slurry dispersed in a solvent in the case of a powder.

The temperature for conducting the contact treatment of the reaction product of the transesterification reaction with the adsorbent C in the production method of the present invention is not particularly limited, but it is preferably from 0 to 150° C. and particularly preferably from 30 to 130° C. The effect of removing the catalyst is insufficient when the reaction temperature is lower than 0° C., and the adsorbent C causes a side reaction in some cases and the purification step is thus complicated when the reaction temperature exceeds 150° C.

The pressure for conducting the contact treatment of the reaction product of the transesterification reaction with the adsorbent C in the production method of the present invention is not particularly limited, and the contact treatment may be conducted in a reduced pressure state or a pressurized state. The pressure is usually from 0.000001 to 10 MPa (absolute pressure).

The time for conducting the contact treatment of the reaction product of the transesterification reaction with the adsorbent C in the production method of the present invention varies depending on the kind of (meth)acrylate, the kind and amount of catalyst used, the temperature for conducting the contact treatment, the method of contact treatment, and the like, but it is usually from 0.1 to 150 hours and preferably from 0.5 to 80 hours.

It is preferable to conduct the contact treatment of the reaction product of the transesterification reaction with the adsorbent C in the production method of the present invention so that zinc which is derived from the catalyst B and remains in the purified product containing the (meth)acrylate is less than 800 ppm, it is more preferable to conduct the contact treatment so that zinc is less than 400 ppm, it is still more preferable to conduct the contact treatment so that zinc is less than 200 ppm, and it is particularly preferable to conduct the contact treatment so that zinc is less than 100 ppm.

In addition, in a case in which the catalyst A is a cyclic tertiary amine having an azabicyclo structure or a salt thereof or a complex thereof, an amidine or a salt thereof or a complex thereof, a compound having a pyridine ring or a salt thereof or a complex thereof, or a compound having a tertiary diamine structure or a salt thereof or a complex thereof, it is preferable to conduct the contact treatment so that nitrogen derived from the catalyst A is less than 200 ppm, it is more preferable to conduct the contact treatment so that nitrogen is less than 150 ppm, and it is still more preferable to conduct the contact treatment so that nitrogen is less than 100 ppm.

In a case in which the catalyst A is phosphines or a salt thereof or a complex thereof, it is preferable to conduct the contact treatment so that phosphorus derived from the catalyst A is less than 400 ppm, it is more preferable to conduct the contact treatment so that phosphorus is less than 300 ppm, and it is still more preferable to conduct the contact treatment so that phosphorus is less than 200 ppm.

The contact treatment of the reaction product of the transesterification reaction with the adsorbent C in the production method of the present invention can be conducted by any method of a batch method, a semi-batch method, a continuous method, a fixed bed method, or a fluidized bed method. As an example of the batch method, the adsorbent C is added to the reaction product obtained by the transesterification reaction of the present invention or the reaction product obtained after the catalyst component is recovered from the reaction product through pressure filtration, and the contact treatment is conducted by stirring the mixture at a predetermined temperature and a predetermined pressure. Thereafter, the adsorbent C is separated as a residue through a filtration operation, and the unreacted monofunctional (meth)acrylate is taken out by stirring the filtrate at a predetermined temperature and a predetermined pressure while allowing an oxygen-containing gas to bubble in the filtrate, this makes it possible to obtain the target (meth)acrylate as a still residue.

As an example of the fixed bed method, the contact treatment can be conducted by a method in which the reaction product obtained by the transesterification reaction of the present invention passes through a column filled with the adsorbent C.

In order to obtain the high-purity target (meth)acrylate from the reaction product obtained by the production method of the present invention, a separation and purification operation may be conducted in which a crystallization operation such as cooling crystallization or concentrating crystallization; a filtration operation such as pressure filtration, suction filtration, or centrifugal filtration; a distillation operation such as single distillation, fractional distillation, molecular distillation, or steam distillation; an extraction operation such as solid-liquid extraction and liquid-liquid extraction; decantation; and the like are combined. A solvent may be used in the separation and purification operation. In addition, a neutralizing agent for neutralizing the catalyst and/or the polymerization inhibitor used in the present invention or an adsorbent other than the adsorbent C, an acid and/or an alkali for decomposing or removing the by-products, activated carbon for improving the color tone, diatomaceous earth for improving the filtration efficiency and filtration rate, and the like may be used.

EXAMPLES

Hereinafter, the present invention will be described more specifically with reference to Examples and Comparative Examples, but the present invention is not limited to these Examples. Incidentally, in the following description, the term "parts" means "parts by mass", the term "%" means "% by mass", and the term "ppm" means "ppm by mass" unless otherwise stated.

The reaction yield in Examples and Comparative Examples was calculated by using the result of quantitative determination of the monohydric alcohol (derived from the monofunctional (meth)acrylate used as a raw material) generated as a by-product as the transesterification reaction proceeded and the following formula. Incidentally, the quantitative determination of monohydric alcohol was conducted by using a high performance liquid chromatograph equipped with a differential refractive index detector (column: Atlantis (Part No. 186003748, column inner diameter: 4.6 mm, column length: 250 mm) manufactured by Nihon Waters K.K., solvent: pure water or 10% by volume aqueous solution of isopropanol) and the internal standard method.

Reaction yield (% by mole)=number of moles of monohydric alcohol generated as by-product as transesterification reaction proceeds/(number of moles of alcohol used as raw material×number of alcoholic hydroxyl groups in alcohol molecule used as raw material)×100

The purification yield in Examples and Comparative Examples was calculated by using the mass of the purified product which contained the target (meth)acrylate and was obtained after subjecting the reaction product after completion of the transesterification reaction to separation and purification operations such as distillation, crystallization, filtration, and the like.

Purification yield (%)=purified product containing target (meth)acrylate (parts)/(molecular weight of (meth)acrylate generated when all alcoholic hydroxyl groups in alcohol used as raw material are (meth)acrylated×number of moles of alcohol used as raw material)×100

In Examples and Comparative Examples, the confirmation that the target (meth)acrylate was contained in the reaction product and the purified product was performed by using a high performance liquid chromatograph equipped with a UV detector (column: ACQUITY UPLC BEH C18 (Part No. 186002350, column inner diameter: 2.1 mm, column length: 50 mm) manufactured by Nihon Waters K.K., detection wavelength: 210 nm, solvent: mixed solvent of 0.03% by mass aqueous solution of trifluoroacetic acid with methanol).

In Examples and Comparative Examples, the quantitative determination of zinc which was derived from the catalyst B and remained in the purified product containing a (meth) acrylate was conducted by using an ICP emission spectrometer (SPECTRO ARCOS SOP manufactured by AMETEK Inc.) and an ICP mass spectrometer (Agilent 7700s manufactured by Agilent Technologies, Inc.).

In addition, in a case in which the catalyst A was a cyclic tertiary amine having an azabicyclo structure or a salt thereof or a complex thereof, an amidine or a salt thereof or a complex thereof, a compound having a pyridine ring or a salt thereof or a complex thereof, or a compound having a tertiary diamine structure or a salt thereof or a complex thereof, the quantitative determination of nitrogen derived from the catalyst A was conducted by using an analyzer for total trace nitrogen (TN-2100H manufactured by Mitsubishi Chemical Analytech Co., Ltd.).

However, it is difficult to quantitatively determine nitrogen derived from the catalyst A from the result obtained by using the analyzer for trace nitrogen in the case of containing a nitrogen atom in the skeleton of alcohol, and the catalyst A was quantitatively determined by the internal standard method using gas chromatography.

Apparatus: GC-1700 manufactured by Shimadzu Corporation
Detector: FID
Carrier gas: helium
Column: TC-5 (0.32 mm ID×30 m, 0.25 μm)
Injection temperature: 250° C.
FID temperature: 250° C.
Column temperature: kept at 80° C. for 5 minutes, then raised to 280° C. at a rate of 10° C./min, and kept at this temperature for 8 minutes.
Injection volume: 1 μL In addition, in a case in which the catalyst A was phosphines or a salt thereof or a complex thereof, the quantitative determination of phosphorus derived from the catalyst A was conducted by using an ICP emission spectrometer (SPECTRO ARCOS SOP manufactured by AMETEK Inc.).

Example 1

Into a 1 liter flask equipped with a stirrer, a thermometer, a gas introduction tube, a rectifying column, and a cooling tube, 69.33 parts (0.51 mole) of pentaerythritol, 690.05 parts (5.30 moles) of 2-methoxyethyl acrylate, 2.038 parts (0.018 mole) of DABCO as the catalyst A, 3.260 parts (0.018 mole) of zinc acetate as the catalyst B, and 1.56 parts (2036 ppm with respect to the total mass of the raw materials charged) of hydroquinone monomethyl ether were charged, and an oxygen-containing gas (5% by volume of oxygen and 95% by volume of nitrogen) was allowed to bubble in the liquid. The pressure in the reaction system was adjusted in a range of from 130 to 760 mmHg while heating and stirring the reaction liquid at a temperature in a range of from 105 to 120° C., and a liquid mixture of 2-methoxyethanol generated as a by-product and 2-methoxyethyl acrylate as the transesterification reaction proceeded was taken out from the reaction system via the rectifying column and the cooling tube. In addition, 2-methoxyethyl acrylate in the same parts by mass as that of the liquid taken out was added to the reaction system at all times. As a result of quantitative determination of 2-methoxyethanol contained in the liquid taken out from the reaction system, the reaction yield reached 88% after 30 hours from the start of heating and stirring, and thus the pressure in the reaction system was returned to normal pressure and taking out of the by-product was terminated as well as heating of the reaction liquid was terminated.

The reaction product thus obtained was cooled to room temperature and the precipitate was separated through pressure filtration, and 17.25 parts of magnesium silicate (KYOWAAD 600 (trade name) manufactured by Kyowa Chemical Industry Co., Ltd.) as the adsorbent C was then added to the reaction product, and the mixture was heated and stirred for 3 hours at normal pressure and an internal temperature in a range of from 75 to 105° C. for the contact treatment. The solid substance containing the adsorbent C was separated through pressure filtration, and the filtrate was then subjected to vacuum distillation for 8 hours at a temperature of from 70 to 95° C. and a pressure in a range of from 0.001 to 100 mmHg while allowing dry air to bubble in the filtrate, thereby separating a distillate containing unreacted 2-methoxyethyl acrylate. As a result of composition analysis of the residue after vacuum distillation using a high performance liquid chromatograph equipped with a UV detector, it has been confirmed that the residue contains pentaerythritol triacrylate and pentaerythritol tetraacrylate as main components. The purification yield calculated by assuming the residue as a purified product was 94%, the content of nitrogen derived from the catalyst A was 5 ppm, and the content of zinc derived from the catalyst B was 0.01 ppm or less. The results are presented in Table 1.

Example 2

Into a 1 liter flask equipped with a stirrer, a thermometer, a gas introduction tube, a rectifying column, and a cooling tube, 86.33 parts (0.34 mole) of dipentaerythritol, 690.05 parts (5.30 moles) of 2-methoxyethyl acrylate, 4.077 parts (0.036 mole) of DABCO as the catalyst A, 6.520 parts (0.036 mole) of zinc acetate as the catalyst B, and 1.63 parts (2061 ppm with respect to the total mass of the raw materials charged) of hydroquinone monomethyl ether were charged, and an oxygen-containing gas (5% by volume of oxygen and 95% by volume of nitrogen) was allowed to bubble in the liquid. The pressure in the reaction system was adjusted in a range of from 250 to 760 mmHg while heating and stirring the reaction liquid at a temperature in a range of from 120 to 145° C., and a liquid mixture of 2-methoxyethanol generated as a by-product and 2-methoxyethyl acrylate as the transesterification reaction proceeded was taken out from the reaction system via the rectifying column and the cooling tube. In addition, 2-methoxyethyl acrylate in the same parts by mass as that of the liquid taken out was added to the reaction system at all times. As a result of quantitative determination of 2-methoxyethanol contained in the liquid taken out from the reaction system, the reaction yield reached 86% after 24 hours from the start of heating and stirring, and thus the pressure in the reaction system was returned to normal pressure and taking out of the by-product was terminated as well as heating of the reaction liquid was terminated.

The reaction product thus obtained was cooled to room temperature and the precipitate was separated through pressure filtration, and 19.45 parts of aluminum silicate (KYOWAAD 700 (trade name) manufactured by Kyowa Chemical Industry Co., Ltd.) as the adsorbent C was then added to the reaction product, and the mixture was heated and stirred for 3 hours at normal pressure and an internal temperature in a range of from 75 to 105° C. for the contact treatment. The solid substance containing the adsorbent C was separated through pressure filtration, and the filtrate was then subjected to vacuum distillation for 8 hours at a temperature of from 70 to 95° C. and a pressure in a range of from 0.001 to 100 mmHg while allowing dry air to bubble in the filtrate, thereby separating a distillate containing unreacted 2-methoxyethyl acrylate. As a result of composition analysis of the residue after vacuum distillation using a high performance liquid chromatograph equipped with a UV detector, it has been confirmed that the residue contains dipentaerythritol pentaacrylate and dipentaerythritol hexaacrylate as main components. The purification yield calculated by assuming the residue as a purified product was 97%, the content of nitrogen derived from the catalyst A was 17 ppm, and the content of zinc derived from the catalyst B was 0.5 ppm or less. The results are presented in Table 1.

Examples 3 to 21 and Comparative Examples 1 to 10

The purified products containing the target (meth)acrylates were obtained by conducting the transesterification reaction and the contact treatment with the adsorbent C in the same manner as in Examples 1 and 2 except that the alcohol, the monofunctional (meth)acrylate, the catalyst A, the catalyst B, and the adsorbent C were changed, and the content of the catalyst A or nitrogen or phosphorus derived from the catalyst A and the content of zinc derived from the catalyst B in the purified products were then measured. In addition, in Examples 11 and 12 and Comparative Example 5 and 6 in which nitrogen was contained in the skeleton of alcohol used, the content of residual catalyst (DABCO) was measured. The results are presented in Tables 1 to 8.

Incidentally, the following abbreviations were used in the tables.

PET: pentaerythritol
MCA: 2-methoxyethyl acrylate
BA: n-butyl acrylate
DABCO: triethylenediamine
DPET: dipentaerythritol
TMP: trimethylolpropane
DTMP: ditrimethylolpropane
GLY: glycerin
DIGLY: diglycerin
XLY: xylitol
NMI: N-methylimidazole
DMAP: N,N-dimethyl-4-aminopyridine
THEIC: tris(2-hydroxyethyl) isocyanurate
Zn(acac)$_2$: zinc acetylacetonate
TEA: triethanolamine
TPP: triphenylphosphine
GLY1EO: alkylene oxide 1 mole adduct of glycerin (dehydrated product of EMULGEN GE-1AS (trade name) manufactured by Kao Corporation)
GLYCARBO: glycerol 1,2-carbonate
POLYGLY: polyglycerol (average degree of polymerization: 6, dehydrated product of polyglycerin #500 manufactured by Sakamoto Yakuhin Kogyo Co., Ltd.)
DEGV: diethylene glycol monovinyl ether
BzOH: benzyl alcohol
MA: methyl acrylate
EA: ethyl acrylate
IBA: isobutyl acrylate
TMHD: N,N,N',N'-tetramethyl-1,6-hexanediamine
KW-600: magnesium silicate ($2MgO.6SiO_2.XH_2O$, KYOWAAD 600 (trade name) manufactured by Kyowa Chemical Industry Co., Ltd.)
KW-700: aluminum silicate ($Al_2O_3.9SiO_2.XH_2O$, KYOWAAD 700 (trade name) manufactured by Kyowa Chemical Industry Co., Ltd.)
KW-2000: magnesium-aluminum composite oxide ($Mg_{0.7}Al_{0.3}O_{1.15}$, KYOWAAD 2000 (trade name) manufactured by Kyowa Chemical Industry Co., Ltd.)

TABLE 1

| | Alcohol | Monofunctional (meth)acrylate | Catalyst A | Catalyst B | Adsorbent C | Amount of adsorbent C used (%) (to purified product) | Content of nitrogen (ppm) | Content of zinc (ppm) |
|---|---|---|---|---|---|---|---|---|
| Example 1 | PET | MCA | DABCO | Zinc acetate | KW-600 | 10 | 5 | 0.01 or less |
| Example 2 | DPET | MCA | DABCO | Zinc acetate | KW-700 | 10 | 17 | 0.5 |
| Example 3 | DPET | MCA | DABCO | Zinc acetate | KW-2000 | 10 | 85 | 1.6 |
| Example 4 | DTMP | MCA | DABCO | Zinc acetate | KW-600 | 10 | 10 | 2.1 |
| Example 5 | GLY | MCA | DABCO | Zinc acetate | KW-700 | 3 | 43 | 6.3 |
| Example 6 | DIGLY | MCA | DABCO | Zinc acetate | KW-700 | 3 | 5 | 2.3 |
| Example 7 | XLY | MCA | DABCO | Zinc acetate | KW-700 | 13 | 98 | 56 |
| Example 8 | PET | BA | DABCO | Zinc propionate | KW-700 | 3 | 40 | 74 |
| Example 9 | PET | MCA | NMI | Zinc acetate | KW-700 | 12 | 10 | 6.0 |
| Example 10 | PET | MCA | DMAP | Zinc acetate | KW-700 | 19 | 18 | 6.6 |

TABLE 2

| | Alcohol | Monofunctional (meth)acrylate | Catalyst A | Catalyst B | Adsorbent C | Amount of adsorbent C used (%) (to purified product) | Content of DABCO (ppm) | Content of zinc (ppm) |
|---|---|---|---|---|---|---|---|---|
| Example 11 | THEIC | MCA | DABCO | Zn(acac)$_2$ | KW-600 | 6 | Lower limit of detection (undetected) | 5.1 |
| Example 12 | TEA | MCA | DABCO | Zinc acetate | KW-700 | 6 | Lower limit of detection (undetected) | 19 |

TABLE 3

| | Alcohol | Monofunctional (meth)acrylate | Catalyst A | Catalyst B | Adsorbent C | Amount of adsorbent C used (%) (to purified product) | Content of phosphorus (ppm) | Content of zinc (ppm) |
|---|---|---|---|---|---|---|---|---|
| Example 13 | TEA | MCA | TPP | Zinc acetate | KW-700 | 3 | 230 | 12 |

TABLE 4

| | Alcohol | Monofunctional (meth)acrylate | Catalyst A | Catalyst B | Adsorbent C | Amount of adsorbent C used (%) (to purified product) | Content of nitrogen (ppm) | Content of zinc (ppm) |
|---|---|---|---|---|---|---|---|---|
| Example 14 | GLY1EO | MCA | DABCO | Zinc acrylate | KW-700 | 5 | 25 | 10 |
| Example 15 | GLYCARBO | MCA | DABCO | Zinc acrylate | KW-700 | 10 | 3 | 0.1 |
| Example 16 | POLYGLY | MCA | DABCO | Zinc acrylate | KW-700 | 11 | 30 | 5.2 |
| Example 17 | TMP | MA | DMAP | Zinc acetate | KW-600 | 28 | 25 | 4.8 |
| Example 18 | TMP | MA | DMAP | Zinc acetate | KW-700 | 28 | 12 | 2.3 |
| Example 19 | DEGV | MA | DABCO | Zinc acrylate | KW-700 | 5 | 4 | 1.1 |

TABLE 4-continued

| | Alcohol | Monofunctional (meth)acrylate | Catalyst A | Catalyst B | Adsorbent C | Amount of adsorbent C used (%) (to purified product) | Content of nitrogen (ppm) | Content of zinc (ppm) |
|---|---|---|---|---|---|---|---|---|
| Example 20 | BzOH | EA | TMHD | Zinc acrylate | KW-700 | 29 | 10 | 2.2 |
| Example 21 | BzOH | IBA | TMHD | Zinc acrylate | KW-700 | 34 | 8 | 1.8 |

TABLE 5

| | Alcohol | Monofunctional (meth)acrylate | Catalyst A | Catalyst B | Adsorbent C | Amount of adsorbent C used (%) (to purified product) | Content of nitrogen (ppm) | Content of zinc (ppm) |
|---|---|---|---|---|---|---|---|---|
| Comparative Example 1 | PET | MCA | DABCO | Zinc acetate | Unused | 0 | 210 | 810 |
| Comparative Example 2 | DPET | MCA | DABCO | Zinc acetate | Unused | 0 | 400 | 1900 |
| Comparative Example 3 | PET | MCA | NMI | Zinc acetate | Unused | 0 | 2600 | 8500 |
| Comparative Example 4 | PET | MCA | DMAP | Zinc acetate | Unused | 0 | 2700 | 8500 |

TABLE 6

| | Alcohol | Monofunctional (meth)acrylate | Catalyst A | Catalyst B | Adsorbent C | Amount of adsorbent C used (%) (to purified product) | Content of DABCO (ppm) | Content of zinc (ppm) |
|---|---|---|---|---|---|---|---|---|
| Comparative Example 5 | THEIC | MCA | DABCO | Zn(acac)$_2$ | Unused | 0 | 1500 | 3600 |
| Comparative Example 6 | TEA | MCA | DABCO | Zinc acetate | Unused | 0 | 1600 | 3600 |

TABLE 7

| | Alcohol | Monofunctional (meth)acrylate | Catalyst A | Catalyst B | Adsorbent C | Amount of adsorbent C used (%) (to purified product) | Content of phosphorus (ppm) | Content of zinc (ppm) |
|---|---|---|---|---|---|---|---|---|
| Comparative Example 7 | TEA | MCA | TPP | Zinc acetate | Unused | 0 | 4200 | 1900 |

TABLE 8

| | Alcohol | Monofunctional (meth)acrylate | Catalyst A | Catalyst B | Adsorbent C | Amount of adsorbent C used (%) (to purified product) | Content of nitrogen (ppm) | Content of zinc (ppm) |
|---|---|---|---|---|---|---|---|---|
| Comparative Example 8 | TMP | MA | DMAP | Zinc acetate | Unused | 0 | 5300 | 15000 |
| Comparative Example 9 | DEGV | MA | DABCO | Zinc acrylate | Unused | 0 | 1800 | 10300 |
| Comparative Example 10 | BzOH | EA | TMHD | Zinc acrylate | Unused | 0 | 1400 | 4000 |

In Examples in which the adsorbent treatment by the adsorbent C of the present invention was conducted, it was possible to obtain a high-quality (meth)acrylate as the amount of impurities which were contained in the purified product and derived from the catalyst was significantly smaller as compared to Comparative Examples in which the adsorption treatment was not conducted.

INDUSTRIAL APPLICABILITY

According to the method of the present invention, it is possible to obtain a high-quality (meth)acrylate containing impurities derived from a catalyst in a significantly small amount from an alcohol and a monofunctional (meth)acrylate. It is possible to suitably use the (meth)acrylate obtained by the method of the present invention in various kinds of industrial applications as a crosslinking component of blended materials such as paints, inks, adhesives, optical applications such as films, sheets, and optical lenses, fillers, and molding materials or a reactive diluent component.

The invention claimed is:

1. A method for producing a (meth)acrylate, the method comprising:
   subjecting a reaction product of a transesterification reaction to contact treatment with the following adsorbent C when producing a (meth)acrylate by subjecting an alcohol and a monofunctional (meth)acrylate to a transesterification reaction using the following catalyst A and the following catalyst B concurrently:
   catalyst A: one or more kinds of compounds selected from the group consisting of a cyclic tertiary amine having an azabicyclo structure or a salt thereof or a complex thereof, an amidine or a salt thereof or a complex thereof, a compound having a pyridine ring or a salt thereof or a complex thereof, and a compound having a tertiary diamine structure or a salt thereof or a complex thereof,
   catalyst B: one or more kinds of compounds selected from the group consisting of a compound containing zinc, and
   adsorbent C: one or more kinds of compounds selected from the group consisting of an oxide and a hydroxide which contain at least one kind among magnesium, aluminum, and silicon.

2. The method for producing a (meth)acrylate according to claim 1, wherein the alcohol is a polyhydric alcohol having three or more alcoholic hydroxyl groups.

3. The method for producing a (meth)acrylate according to claim 1, wherein the alcohol is any of trimethylolethane, trimethylolpropane, glycerin, an alkylene oxide adduct of glycerin, tris (2-hydroxyethyl) isocyanurate, triethanolamine, ditrimethylolethane, ditrimethylolpropane, diglycerin, an alkylene oxide adduct of diglycerin, pentaerythritol, an alkylene oxide adduct of pentaerythritol, xylitol, dipentaerythritol, an alkylene oxide adduct of dipentaerythritol, D-sorbitol, or polyglycerin.

4. The method for producing a (meth)acrylate according to claim 1, wherein the alcohol is pentaerythritol or dipentaerythritol.

5. The method for producing a (meth)acrylate according to claim 1, wherein the monofunctional (meth)acrylate is any of methyl acrylate, ethyl acrylate, n-butyl acrylate, i-butyl acrylate, or 2-methoxyethyl acrylate.

6. The method for producing a (meth)acrylate according to claim 1, wherein the monofunctional (meth)acrylate is 2-methoxyethyl acrylate.

7. The method for producing a (meth)acrylate according to claim 1, wherein the catalyst A is any one of quinuclidine, 3-hydoxyquinuclidine, triethylenediamine, 2-(hydroxymethyl)triethylenediamine, N-methylimidazole, or N,N,N',N'-tetramethyl-1,6-hexanediamine.

8. The method for producing a (meth)acrylate according to claim 1, wherein the catalyst B is a compound which contains zinc and is represented by the following general formula (4) or the following general formula (5):

[Chemical formula 4]

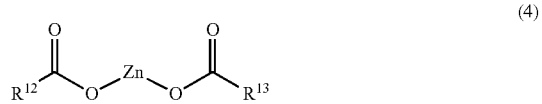

(4)

wherein $R^{12}$ and $R^{13}$ may be the same as or different from each other, are a linear or branched alkyl group having from 1 to 20 carbon atoms, a linear or branched alkyenyl group having from 1 to 20 carbon atoms, an aryl group having from 6 to 24 carbon atoms, or a cycloalkyl group having from 5 to 20 carbon atoms, and may have a substituent, and wherein $R^{12}$ and $R^{13}$ do not have a halogen atom;

[Chemical formula 5]

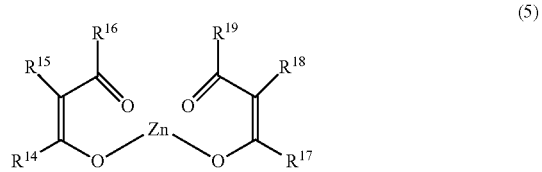

(5)

wherein $R^{14}$, $R^{15}$, $R^{16}$, $R^{17}$, $R^{18}$, and $R^{19}$ may be the same as or different from one another, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may having a substituent, and further wherein $R^{15}$ and/or $R^{18}$ may be a hydrogen atom.

9. The method for producing a (meth)acrylate according to claim 1, wherein the catalyst A is triethylenediamine and the catalyst B is a compound which contains zinc and is represented by the general formula (4).

10. The method for producing a (meth)acrylate according to claim 1, wherein the adsorbent C is either one of magnesium silicate or aluminum silicate.

* * * * *